United States Patent
Hakim

(10) Patent No.: US 9,700,507 B1
(45) Date of Patent: *Jul. 11, 2017

(54) LOTION TO HELP WITH DRY SCALP SYMPTOMS AND METHODS OF USE

(71) Applicant: Noha N. Hakim, Easton, PA (US)

(72) Inventor: Noha N. Hakim, Easton, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/166,831

(22) Filed: May 27, 2016

(51) Int. Cl.
  *A61K 8/97* (2017.01)
  *A61K 8/92* (2006.01)
  *A61K 8/20* (2006.01)
  *A61K 8/73* (2006.01)
  *A61Q 19/00* (2006.01)
  *A61Q 5/00* (2006.01)
  *A61K 8/36* (2006.01)
  *A61K 8/99* (2017.01)
  *A61K 8/34* (2006.01)

(52) U.S. Cl.
  CPC .............. *A61K 8/97* (2013.01); *A61K 8/20* (2013.01); *A61K 8/34* (2013.01); *A61K 8/36* (2013.01); *A61K 8/732* (2013.01); *A61K 8/922* (2013.01); *A61K 8/99* (2013.01); *A61Q 19/007* (2013.01)

(58) Field of Classification Search
  None
  See application file for complete search history.

(56) References Cited

U.S. PATENT DOCUMENTS

| | | | | |
|---|---|---|---|---|
| 4,505,902 A | * | 3/1985 | Millard | A61K 8/922 424/735 |
| 4,943,432 A | * | 7/1990 | Biener | A61K 8/19 424/647 |
| 5,705,172 A | * | 1/1998 | Efron | A61F 7/02 424/402 |
| 5,866,145 A | * | 2/1999 | Stavroff | A61K 8/03 424/401 |
| 6,582,709 B1 | * | 6/2003 | Maor | A61K 8/27 424/401 |
| 6,723,309 B1 | * | 4/2004 | Deane | A61K 8/416 424/70.1 |
| 8,486,463 B1 | * | 7/2013 | Brieva | A61K 8/97 424/725 |
| 2006/0134238 A1 | * | 6/2006 | Dnyaneshwar | A61K 36/886 424/744 |
| 2008/0175928 A1 | * | 7/2008 | Jochim | A61K 8/0212 424/727 |
| 2008/0286390 A1 | * | 11/2008 | Tanyi | A61K 8/922 424/744 |
| 2011/0212184 A1 | * | 9/2011 | Samelson | A61K 8/044 424/537 |

OTHER PUBLICATIONS

Proksch, Ehrhardt, et al. "Bathing in a magnesium-rich Dead Sea salt solution improves skin barrier function, enhances skin hydration, and reduces inflammation in atopic dry skin." International journal of dermatology 44.2 (2005): 151-157.*
Active Micro Technologies, LLC, "Leucidal® Liquid Complete," Technical Data Sheet (Version 4), Aug. 2016.*

* cited by examiner

*Primary Examiner* — Bethany Barham
*Assistant Examiner* — Peter Anthopolos
(74) *Attorney, Agent, or Firm* — Gary P. Topolosky

(57) ABSTRACT

This invention is a natural scalp lotion that exploits the benefits of Dead Sea salt by adding it to a base of organic aloe vera juice, organic coconut oil, castor oil, sweet almond oil, olive oil, NF emulsified wax (vegetable based), potato starch, and apple cider vinegar. It also includes several 100% pure essential oils/extracts, and preservatives.

9 Claims, No Drawings

LOTION TO HELP WITH DRY SCALP SYMPTOMS AND METHODS OF USE

BACKGROUND

The scalp skin contains hair follicles and sebaceous glands that secrete a natural oil slightly acidic called sebum to protect the skin from becoming too dry.

Dry scalp can be caused by the application of soap, strong detergents, cold weather, hair products build up, hard water, and diet.

The signs and symptoms that caused by dry scalp such as itching, dandruff and thinning hair may be helped by applying natural remedies to restore the pH on scalp to encourage the balanced sebum production and help scalp skin to recover from the effects of high pH shampoos, conditioners, and the buildup left behind other hair products.

FIELD OF THE INVENTION

This invention relates to lotions for use by humans to help with symptoms caused by dry scalp skin. Particularly, it relates to lotions for hydrating the scalp and brings the scalp skin to a balanced pH acid mantle that will encourage the sebaceous glands to produce balanced sebum amount for healthy scalp and hair. It will also help to get rid of symptoms such as itching, dandruff or thinning hair. Preferred compositions will be sold under the SeaLand Cosmetics™ brand.

The SeaLand Cosmetics Scalp Lotion is a unique combination of salt from the Dead Sea and the earth's natural ingredients such as Organic Aloe Vera, Organic Coconut oil, Olive oil, Castor oil, sweet almond oil, Apple Cider Vinegar, pure essential oils, this formulation will aid to hydrate the scalp area of the human body and keep the skin at its normal acid mantle pH (4.5-6).

To assure safety of the product, SeaLand Cosmetics uses in the scalp lotion a combination of the natural preservative Leucidal liquid (plant-based) and phenoxyethanol which is a nature identical chemical that can be found in green tea and produced by treating phenol with ethylene oxide in an alkaline medium that reacts to form a pH balanced ingredient. This synthetically produced commercial ingredient does not release formaldehyde or cause health risks and assures the safety of the product. One commercial product is Optiphen® Plus and it is used with <1.0% in the scalp formulation of this invention. Should Optiphen® Plus no longer be commercially available, substantially equivalent alternatives may be substituted therefore.

RELATED ART

Dead Sea salt, as removed from waters from the Dead Sea water, is a known component for various preferred end uses.

Biener U.S. Pat. No. 4,943,432 added such salts to magnesium halide, several alkaline earth metal salts and other cations as part of a composition for treating psoriasis.

Stravroff et al. U.S. Pat. No. 5,866,145 mixed Dead Sea salts with some silicone oils and fragrances to serve as a moisturizing body "polisher".

Maor et al. U.S. Pat. No. 6,582,709 discloses a pharmaceutical cream composition for the treatment of skin disorders, said composition including about 1-6 wt. % Dead Sea mud as an active ingredient.

Lucenta U.S. Published Application No. 20110229419 mixed Dead Sea salt with sodium chloride for the prevention and healing of canker sores.

Finally, Samuelson et al. U.S. Pat. No. 9,050,273 discloses using ultra fine Dead Sea mineral compounds in compositions for use in bath and body products.

The Dead Sea is one of the most saline lakes in the world. It lies between the hills of Judaea to the west and the Trans-Jordanian plateaus to the east. The Jordan River flows from the north into the Dead Sea. About 2.5 million years ago, heavy stream flow into the lake deposited thick sediments containing shale, clay, sandstone, rock salt, and gypsum. After this, strata of clay, marl, soft chalk, and gypsum fell upon layers of sand and gravel.

Having no outlet, the Dead Sea is a "terminal lake" meaning that it loses huge amounts of water by evaporation in the hot dry air. The water has evaporated faster than it has been replenished by precipitation over the last 10,000 years. That results in the lake gradually shrinking to its present form. Because of this, bare deposits cover the Dead Sea valley to a thickness of 1 to 4 miles (1.6 to 6.4 km). This water evaporation has also resulted in high concentrations of salts and minerals in a unique composition particularly rich in magnesium, sodium, potassium, calcium, bromide and various other minor anions such as, e.g., sulfate.

The concentration of salt increases as one descends toward the bottom of the Dead Sea. Down to 130 feet (40 m), the temperature varies from 66 to 98° F. (19 to 37° C.), and the salinity is slightly less than 300 parts per thousand. At this depth, the water is particularly rich in sulfates and bicarbonates. There is a transition zone located between 130 and 330 feet (40 and 100 m). The lower waters below 330 ft (100 m) have a uniform temperature of about 72° F. (22° C.) and a higher degree of salinity (approximately 332 parts per thousand). This lower water contains hydrogen sulfide along with strong concentrations of magnesium, potassium, chlorine, and bromine. Below that level, the deepest waters are saturated with sodium chloride that precipitates to the bottom.

The lower waters of the Dead Sea are fossilized; they remain permanently on the bottom because they are very salty and dense. The upper waters date from a few centuries A.D.

The Dead Sea's mineral composition differs from that of ocean water, the salt in most oceans is approximately 85% sodium chloride while Dead Sea salt is only 12-18% sodium chloride. An analysis of major ion concentrations in the water of the Dead Sea gave the following results. (Reference 1)

The major ions in Dead Sea water are:

| Ion | Concentration (mg/L) |
| --- | --- |
| Chloride and Bromide | 230,400 |
| Magnesium | 45,900 |
| Sodium | 36,600 |
| Calcium | 17,600 |
| Potassium | 7,800 |

The Dead Sea's overall salt concentration is 340 g/L according to Reference 1. One study concluded that the high concentration of Mg in Dead Sea salt made it instrumental in improving skin hydration and reducing inflammation (Reference 2). According to Reference 3, the high concentration of bromide and magnesium in Dead Sea salt can cleanse and detoxify the skin and body. References 4 and 5 both address bathing in a Mg-rich, Dead Sea salt solution.

REFERENCES

1. Kuehl B L, Fyfe K S, Shear N H (March 2003). "*Cutaneous cleansers*". Skin Therapy Lett 8 (3): 1-4. PMID 12858234.

2. Pierce J D Jr, Zeng X N, Aronov E V, Preti G, Wysocki C J (August 1995). "*Cross-adaptation of sweaty-smelling 3-methyl-2-hexenoic acid by a structurally similar, pleasant-smelling odorant*". Chem Senses 20 (4): 401-11. doi:10.1093/chemse/20.4.401. PMID 8590025.
3. Ma'or, Zeev et al. "*Antimicrobial properties of Dead Sea black mineral mud*", International Journal of Dermatology, May 2006. Retrieved on 2008 Apr. 13.
4. Proksch, Ehrhardt M D, PhD et al. "*Bathing in a magnesium-rich Dead Sea salt solution improves skin barrier function, enhances skin hydration, and reduces inflammation in atopic dry skin*", International Journal of Dermatology, February 2005. Retrieved on 2008 Apr. 13.
5. Ehrhardt, Proksch; Nissen, H P; Bremgartner, M; Urquhart, C. "*Bathing in a magnesium-rich Dead Sea salt solution: follow-on review*". International Journal of Dermatology 46 (2): 177-179. doi:10.1111/j.1365-4632.2005.02079.x. PMID 15689218.

SUMMARY OF THE INVENTION

A first object of the invention is to create a natural formulation that contains 6% Dead Sea salt for humans use to get rid of symptoms caused by dry scalp.

A second object is to create a pH-balanced scalp formulation by including natural ingredients such as organic Aloe Vera juice, organic coconut oil, castor oil, sweet almond oil, apple cider vinegar and pure essential oils such as alfalfa, licorice, tea tree and rosemary to work in harmony to help moisturizing human skin in the scalp or upper head area.

A Third object is to assure the safety of the product by adding natural plant based preservative (Leucidal liquid) and phenoxyethanol (Optiphen® Plus: the listed ingredients of which include phenoxyethanol, caprylyl glycol and sorbic acid). Also natural preservatives included in the organic aloe vera juice (potassium sorbate and citric acid). Also the product doesn't contain any ingredients with Triclosan, Phthalates, Soy or Gluten.

DESCRIPTION OF PREFERRED EMBODIMENTS

Ideally, the composition of this scalp lotion includes the following in addition to its main novel ingredient of Dead Sea salt.

Aloe Vera Juice:

It is used instead of water as a diluent; it soothes the skin and moisturizes the dry scalp. It has cleansing enzymes that eliminates the dead skin cell flakes and dandruff. Also it helps to expel the bacteria and other fatty deposits which clog the hair follicles.

Organic Coconut Oil:

Coconut oil has wide benefits to skin and hair. It moisturizes scalp skin and may help correct redness and irritation caused by dry scalp.

Castor Oil:

Castor oil penetrates deep into the skin, softens and hydrates it. It carries ricinoleic acid and omega-6 essential fatty acids, which accelerate blood circulation to the scalp and hence increasing hair growth.

Olive Oil:

Olive oil is composed mainly of the mixed triglyceride esters of Oleic and palmitic acids and other fatty acids. It also contains other nutrients like vitamins A and E that help to moisture scalp and reduce the damage done by hair care products (chemical based) or overuse of styling products.

Also when olive oil blends well with coconut oil before adding it to the formula, it decreases the chance of the organic coconut oil to convert back to its solid state in cold environment.

Sweet Almond Oil:

The oil is rich in Vitamin E, monounsaturated fatty acids, proteins, potassium and zinc, besides a number of other minerals such as Calcium and Magnesium which are essential to maintain healthy scalp and hair.

NF Emulsifying Wax (Vegetable Based):

It is used to form emulsion between water and oil ingredients by attracting them to different portions of its structure (hydrophilic for water molecules and hydrophobic for oil molecules).

Apple Cider Vinegar:

It keeps the pH of this scalp lotion on the acidic side.

Potato Starch:

It is added for thickening the lotion and adds a soft touch to the lotion.

Preservatives:

One preferred set of preservatives for use in this product consists of:

(i) 1.4% natural preservative called Leucidal Liquid, it is a product derived from radishes fermented with *Leuconostoc kimchii*, lactic acid bacteria that has traditionally been used to make kimchi, this product consists of an isolated peptide that is secreted from the bacteria during the fermentation process that has been shown to have antimicrobial benefits. Leucidal® Liquid is accepted by ECOcert as an ingredient in certified organic cosmetics. and (ii) 0.6% Phenoxyethanol. Though the latter is not natural, it is the only synthetic preservative which: doesn't release formaldehyde, works well with formulas having a pH less than 6 and which causes the least (i) skin irritation. One representative off-the-shelf preservative is a product called Optiphen® Plus, the listed ingredients of which include phenoxyethanol, caprylyl glycol and sorbic acid.

Pure Essential Oils & Extracts:

Alfalfa Extract:

Alfalfa chlorophyll and its high Vitamin A content help to cure dry skin problem. It also contains silica and high content of Vitamins B, E and C, which are beneficial in improving the circulation of blood in the scalp and help with the proper growth and health of hair.

Licorice Extract:

It is rich in choline, B-complex vitamins, phosphorus, potassium and amines which promote healthy scalp and hair. It soothes the dry scalp and prevents various scalp conditions like dandruff and scabs.

Tea Tree Essential Oil:

It has antibacterial and antiseptic activities, it moisturizes the hair and scalp reducing and eliminating dryness and itching.

Rosemary Essential Oil:

The oil is rich in antioxidants and essential acids that help improve scalp conditions such as dandruff, as it balances scalp's oil secretions.

EXAMPLE

A scalp-hydrating lotion is in a 2 oz. container. A main formula for that lotion according to this invention consists of:

60% Organic Aloe Vera Juice
8% Organic Coconut oil
7% Castor oil
6% Dead Sea salt 5% Olive oil
4% Sweet Almond oil
4% NF Emulsified Wax (Vegetable Based)
2% Potato starch
1.4% Leucidal Liquid
1% Apple Cider vinegar
1% pure Essential oils and Extracts (Alfalfa, Licorice, Tea Tree, Rosemary)
0.6% Phenoxyethanol (Optiphen® Plus)

It should be noted that the organic Aloe Vera juice used in this formula contains natural preservatives, particularly potassium sorbate and citric acid.

Preferred embodiments of this scalp lotion offer a pH-balanced formula (accomplished by adding together apple cider vinegar, sweet almond oil and the pure essential oils). The aforesaid combination of components achieves a pH in the range of about 3-5.

The aforementioned ingredients are mixed altogether and bottled in a 2 oz. plastic container with flip top style dispenser lid. Directions for use of this invention are as follows:

First shake the container/bottle before applying to the user's scalp after that area has been cleaned and dried. Massage it to the scalp skin, no need to rinse it and can be applied as much as needed.

Needless to say, keep the container tightly closed when not in use.

If the user suspects an allergic reaction, he/she should discontinue further uses and consult a physician.

While the invention has been described with a certain degree of particularity; it is manifest that many changes may be made in the arrangement of components without departing from the spirit and scope of this disclosure. It is understood that the invention is not limited to the embodiments set forth herein for purposes of exemplification, but is to be limited only by the scope of the attached claim or claims.

What is claimed is:

1. A lotion for use on a scalp region of a human for hydrating scalp region, said lotion comprising:
    (a) about 55-65 wt. % aloe vera juice,
    (b) about 6-10 wt. % coconut oil,
    (c) about 5-9 wt. % castor oil,
    (d) about 4-8 wt. % Dead Sea salt,
    (e) about 4-6 wt. % olive oil,
    (f) about 3-5 wt. % sweet almond oil,
    (g) about 3-5 wt. % emulsified wax,
    (h) about 1-3 wt. % potato starch, and
    (i) about 0.5-1.5 wt. % apple cider vinegar.

2. The lotion of claim 1, wherein said lotion further includes:
    (j) about 1.4-2.6 wt. % of a preservative.

3. The lotion of claim 2 wherein the preservative consists essentially of:
    (i) about 1-1.8% *leuconostoc*/radish root ferment filtrate and *lactobacillus* and *cocos nucifera* (coconut) fruit extract by weight of the lotion; and
    (ii) about 0.4-0.8% phenoxyethanol by weight of the lotion.

4. The lotion of claim 3 wherein the preservative consists essentially of:
    (i) about 1.4 wt. % *leuconostoc*/radish root ferment filtrate and *lactobacillus* and *cocos nucifera* (coconut) fruit extract by weight of the lotion; and
    (ii) about 0.6 wt. % phenoxyethanol and caprylyl glycol and sorbic acid by weight of the lotion.

5. The lotion of claim 1, which further includes a blend of alfalfa extract, licorice extract, tea tree oil and rosemary oil.

6. The lotion of claim 5 wherein said lotion comprises:
    (a) about 60 wt. % aloe vera juice,
    (b) about 8 wt. % coconut oil,
    (c) about 7 wt. % castor oil,
    (d) about 6 wt. % Dead Sea salt,
    (e) about 5 wt. % olive oil,
    (f) about 5 wt. % sweet almond oil,
    (g) about 4 wt. % emulsified wax,
    (h) about 2 wt. % potato starch,
    (i) about 1 wt. % apple cider vinegar, and
    (j) about 1 wt. % of the blend of alfalfa extract, licorice extract, tea tree oil and rosemary oil.

7. The lotion of claim 1 wherein the pH of the lotion is 4.0+/−1.0.

8. A lotion for applying to a human scalp for achieving healthy scalp and hair, said lotion comprising:
    (a) about 55-65 wt. % aloe vera juice,
    (b) about 6-10 wt. % coconut oil,
    (c) about 5-9 wt. % castor oil,
    (d) about 4-8 wt. % Dead Sea salt,
    (e) about 4-6 wt. % olive oil,
    (f) about 3-5 wt. % sweet almond oil,
    (g) about 3-5 wt. % emulsified wax,
    (h) about 1-3 wt. % potato starch,
    (i) about 0.5-1.5 wt. % apple cider vinegar,
    (j) about 0.5-1.5 wt. % of a blend of alfalfa extract, licorice extract, tea tree oil and rosemary oil, and
    (k) about 1.4-2.6 wt. % of a preservative.

9. The lotion of claim 8 wherein the preservative consists essentially of:
    (i) about 1-1.8% *leuconostoc*/radish root ferment filtrate and *lactobacillus* and *cocos nucifera* (coconut) fruit extract by weight of the lotion; and
    (ii) about 0.4-0.8% phenoxyethanol and caprylyl glycol and sorbic acid by weight of the lotion.

* * * * *